United States Patent [19]

Teng

[11] Patent Number: 4,571,393

[45] Date of Patent: Feb. 18, 1986

[54] 3-PHENOXY-1-AZETIDINECARBOXA-MIDES

[75] Inventor: Lina C. Teng, Richmond, Va.

[73] Assignee: A. H. Robins Company, Incorporated, Richmond, Va.

[21] Appl. No.: 664,036

[22] Filed: Oct. 23, 1984

Related U.S. Application Data

[63] Continuation-in-part of Ser. No. 409,476, Aug. 19, 1982, abandoned.

[51] Int. Cl.$^4$ .................. C07D 205/04; A61K 31/395
[52] U.S. Cl. .................. 514/210; 260/239 A
[58] Field of Search ........................................ 514/210

[56] References Cited

U.S. PATENT DOCUMENTS

| | | | |
|---|---|---|---|
| 3,094,518 | 6/1963 | Testa et al. ..................... | 260/239 A |
| 4,133,881 | 1/1979 | Cale, Jr. ............................. | 514/210 |
| 4,226,861 | 10/1980 | Cale, Jr. ............................. | 514/210 |
| 4,379,151 | 4/1983 | Cale, Jr. ............................. | 514/210 |
| 4,505,907 | 3/1985 | Wright et al. ..................... | 514/210 |

*Primary Examiner*—Donald G. Daus
*Assistant Examiner*—William A. Teoli, Jr

[57] ABSTRACT

3-Phenoxy-1-azetidinecarboxamides having the formula

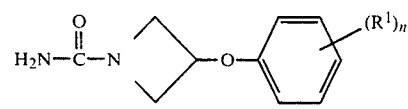

wherein $R^1$ is selected from the group consisting of hydrogen, fluoro, loweralkyl, loweralkoxy, trifluoromethyl, acetyl or aminocarbonyl having prolonged anticonvulsant activity are disclosed.

3 Claims, No Drawings

3-PHENOXY-1-AZETIDINECARBOXAMIDES

This application is a continuation-in-part of U.S. application Ser. No. 409,476 filed Aug. 19, 1982 now abandoned.

BACKGROUND OF THE INVENTION

1. Field of Invention

The present invention relates to novel 3-phenoxy-1-azetidinecarboxamides which exhibit anticonvulsant activity in animals and are effective in the treatment of epilepsy in humans. 2. Description of the Prior Art N-loweralkyl-3-phenoxy-1-azetidinecarboxamides are disclosed in U.S. Pat. No. 4,226,861 as having anticonvulsant activity and useful in the treatment of epilepsy.

The compounds of the present invention were discovered as metabolites in the bloodstream of animals treated with the foregoing N-loweralkyl analogs and have been found to have greater longevity in the bloodstream and greater persistence in their anticonvulsant effect than the corresponding N-loweralkyl analogs.

OBJECTS AND SUMMARY OF THE INVENTION

The 3-phenoxy-1-azetidinecarboxamides of the present invention have the formula:

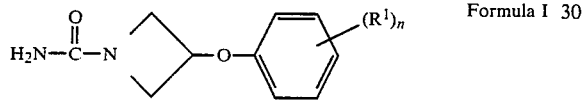

Formula I wherein;
  $R^1$ is selected from the group consisting of hydrogen, fluoro, loweralkyl, loweralkoxy, trifluoromethyl, acetyl or aminocarbonyl; and
  n is selected from 1 to 3 inclusive wherein $R^1$ may be the same or different.

In the further definition of symbols in Formula I and where they appear elsewhere throughout this specification and in the claims, the terms have the following significance.

The term "loweralkyl" includes straight and branched chain hydrocarbon radicals of up to eight carbon atoms inclusive and is exemplified by such groups as methyl, ethyl, propyl, isopropyl, butyl, isobutyl, tertiary butyl, amyl, isoamyl, hexyl, heptyl, octyl and the like.

The term "loweralkoxy" has the formula O-loweralkyl.

The compounds of Formula I are useful because of their pharmacological action on the central nervous system.

The procedure for testing the compounds for their anticonvulsant activity and comparison with prior art compounds is based on evaluation techniques published by Swinyard, E. A. in EPILEPSIA 10: 107–19 (1969) and in J. PHARMAC. EXPTL. THERAP. 106: 319–30 (1952) as explained in greater detail below.

Sequence of reaction in preparation of compounds of Formula I is diagrammed in Chart I. The preparation of certain of the compounds of Formula II is also disclosed in copending U.S. application Ser. No. 312,046 filed Oct. 16, 1981, now U.S. Pat. No. 4379151. Compounds of Formula III wherein $R^2$ is α-methylbenzyl or diphenylmethyl are prepared by reacting compounds of Formula IV and V at temperatures up to about 80°–100° C. for periods of 2–5 hr. in dimethylformamide. Compounds of Formula II are prepared by hydrogenolysis of compounds of Formula III, usually in the presence of a lower-alkanol solvent, ethanol being preferred. The rate of hydrogenolysis is dependent somewhat on time and temperature, a higher temperature generally decreasing the time required for complete hydrogenolysis. Typical times vary from about 3 hr to about 24 hr at temperatures of 50°–90° C.

CHART I

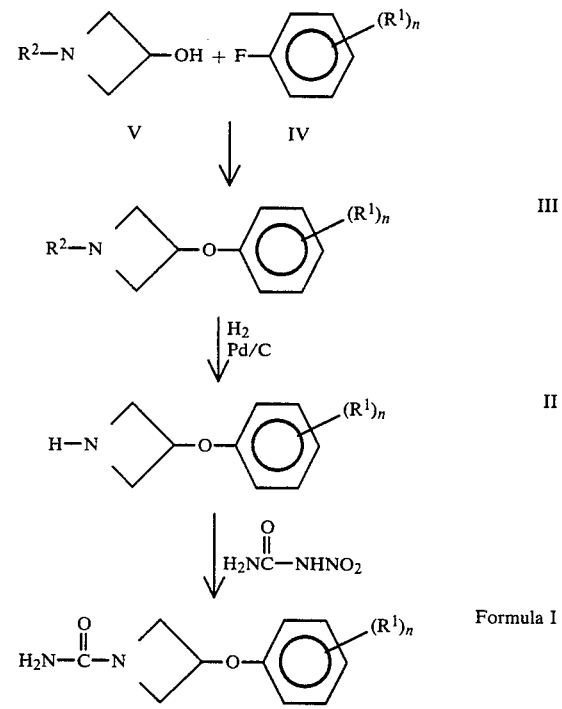

$R^2$ = α-methylbenzyl or diphenylmethyl.
$R^1$ = hydrogen, loweralkyl, loweralkoxy, fluorine, trifluoromethyl, acetyl or aminocarbonyl.
n is 1–3 wherein $R^1$ may be the same or different.

In the final step, compounds of Formula II are reacted with nitrourea in solution to give the products (I) conveniently, for example, in a mixture of ethanol and methylene chloride or acetone at room temperature, usually until analysis indicates substantial reaction has occurred. Products are isolated by evaporation of reaction solvent, partitioning with water and an organic solvent for the product and evaporating the organic solvent layer and recrystallizing.

When compounds of Formulas II or III are isolated as an acid addition salt in synthesis procedure and it is desirable to obtain the free base, the salts are partitioned in a dilute aqueous basic solution and a suitable organic solvent for the free base and then the free base is isolated by dryng and evaporating the organic solvent.

Preparations 1–18 illustrate the preparation of compounds of Formula II and their precursors and the examples illustrate the final conversion to compounds of Formula I. It will be apparent to those skilled in the art that modifications may be practiced without departing from the purpose and intent of the disclosure.

PREPARATION 1

3-(3-chlorophenoxy)-1-(α-methylbenzyl)azetidine Oxalate 1-(α-Methylbenzyl)-3-hydroxyazetidine maleate (393 g., 1.3 moles) was partitioned in dilute potassium hydroxidebenzene. The separated dried benzene solution was concentrated, the residual oil dissolved in 250 ml. of dimethylformamide and added dropwise to a stirred suspension of 53 g. (1.1 moles) of 50% sodium hydride in 750 ml. of dimethylformamide at 90° C. The mixture was heated at 90° C. for 1 hr. and 130.5 g. (1-mole) of 3-chlorofluorobenzene added dropwise at 90° C. The mixture was refluxed for 3 hrs., cooled and partitioned between isopropyl ether and dilute sodium hydroxide. The isopropyl ether solution was dried, concentrated, and the residue added to 1200 ml. of isopropyl alcohol containing 90 g. (1 mole) of oxalic acid. The oxalate salt was recrystallized from ethanol. Yield 263 g. (69%); m.p. 141°–144° C.

Analysis: Calculated for $C_{19}H_{20}ClNO_5$: C,60.40; H,5.34; N,3.71. Found: C,60.19; H,5.55; N,3.60.

PREPARATION 2

1-(α-Methylbenzyl)-3-(4-trifluoromethylphenoxy)azetidine

The maleate salt of 1-(α-methylbenzyl)-3-hydroxyazetidine (78.6 g., 0.20 mole) was partitioned between benzene and dilute sodium hydroxide, the benzene layer dried, filtered, and concentrated at reduced pressure. The residue was dissolved in 100 ml. of dry dimethylformamide and added at a rapid dropwise rate, to a stirring suspension of 10.1 g. (0.22 mole) of sodium hydride (50% in mineral oil) in 150 ml. of dry dimethylformamide at 90° C. The solution was heated at 90° C. for one hour and then treated dropwise with 32.0 g. (0.20 mole) of 4-trifluoromethylfluorobenzene. The solution was refluxed for three hours. The cooled solution was partitioned between water and isopropyl ether, and the ether layer extracted with dilute hydrochloric acid. The aqueous acid layer was made basic with concentrated sodium hydroxide and ice, and extracted with isopropyl ether. The ether layer was concentrated and the residue distilled at 150°–160° C./0.2 mm. to give 25.6 g of product.

Analysis: Calculated for $C_{18}H_{18}F_3NO$: C,67.28; H,5.65; N,4.36. Found: C,67.27; H,5.84; N,4.34.

Preparations 3 to 7 were prepared according to the procedures set forth in detail in Preparations 1 and 2 by reacting 1-(α-methylbenzyl)-3-azetidinol with the appropriately substituted fluorobenzene. The physical constants are shown in Table I.

TABLE I $C_6H_5(CH_3)CH-N\diagdown\diagup-O-\diagup\diagdown-R$

| Preparation | R | M.p. (b.p.) °C. | Salt |
|---|---|---|---|
| 3 | 2-CONH₂ | 148–52 | — |
| 4 | 4-CN | 65–8 | — |
| 5 | 3-CF₃ | 150–3 | (COOH)₂ |
| 6 | 2-CF₃ | 162–3 | (COOH)₂ |
| 7 | 3-CN | ¹(185–90) | — |

The analytical data of Preparations 3 to 7 are shown in Table II.

TABLE II

| Preparation | Empirical Formula | Calculated C | Calculated H | Calculated N | Found C | Found H | Found N |
|---|---|---|---|---|---|---|---|
| 3 | $C_{18}H_{20}N_2O_2$ | 72.95 | 6.80 | 9.45 | 72.56 | 6.78 | 9.32 |
| 4 | $C_{18}H_{18}N_2O$ | 77.67 | 6.52 | 10.06 | 77.61 | 6.53 | 10.01 |
| 5 | $C_{20}H_{20}F_3NO_5$ | 58.39 | 4.90 | 3.41 | 57.99 | 4.97 | 3.39 |
| 6 | $C_{20}H_{20}F_3NO_5$ | 58.39 | 4.90 | 3.41 | 58.15 | 4.89 | 3.37 |
| 7 | $C_{18}H_{18}N_2O$ | 77.67 | 6.52 | 10.06 | 77.32 | 6.54 | 9.87 |

PREPARATION 8

3-[1-(α-Methylbenzyl)-3-azetidinyloxy]benzamide Oxalate

3-[1-(α-Methylbenzyl)3-azetidinyloxy]benzonitrile (50.0 g., 0.18 mole) in 500 ml of t-butyl alcohol was treated with 50.0 g. of finely ground potassium hydroxide. The mixture was stirred at reflux for 30 min. Ice and water were added to the reaction mixture and the organic layer was separated and dried over sodium sulfate. The dried filtered solution was concentrated at reduced pressure. The residue was dissolved in methanol and treated with an equivalent of oxalic acid, and the oxalate salt was recrystallized from ethanol to give 11.4 g. (16%) of product, (m.p. 145° C.).

Analysis: Calculated for $C_{20}H_{22}N_2O_6$: C,62.17; H,5.74; N,7.25. Found: C,62.17; H,5.80; N,7.20.

PREPARATION 9

4-[1-(α-Methylbenzyl)-3-azetidinyloxy]benzamide

To 45.0 g. (0.16 mole) of 4-[1-(α-methylbenzyl)-3-azetidinyloxy]benzonitrile in 500 ml of t-butyl alcohol was added 45.0 g. of finely ground potassium hydroxide. The mixture was stirred and refluxed for 30 minutes. Ice and water were added and a thick white solid separated. The solid was recrystallized from toluene to give 30.0 g. (63%) of product melting at 174°–178° C.

Analysis: Calculated for $C_{18}H_{20}N_2O_2$: C,72.05; H,6.80; N,9.45. Found: C,73.06; H,6.79; N,9.44.

PREPARATION 10

1-Diphenylmethyl-3-phenoxyazetidine

To a stirred suspension of 8.6 g. (0.22 mole) of sodium amide in 100 ml. of dry toluene was added 18.2 g. (0.2 mole) of phenol in 50 ml. of dry toluene. After stirring for 2 hrs. at 60° C. the pot temperature was raised to 80° C. and a solution of 1-diphenylmethyl-3-methylsulfonyloxyazetidine (63.4 g., 0.2 mole) in 200 ml. of dry toluene was added dropwise. After an additional 2 hrs. at 80° C. the cooled mixture was treated with water, the toluene layer was extracted with dilute sodium hydroxide solution, dried and concentrated at reduced pressure. The residue was crystallized twice from a water-isopropanol mixture. The free base melted at 83°–85° C.

Analysis: Calculated for $C_{22}H_{21}NO$: C,83.78; H,6.71; N,4.44. Found: C,83.69; H,6.81; N,4.41.

PREPARATION 11

3-(Phenoxy)azetidine Methanesulfonate

A 200 ml. solution of 7.8 g (0.025 mole) of 1-diphenylmethyl-3-phenoxyazetidine in ethanol was treated with 20% Pd (OH)₂ on carbon and hydrogenated for 23 hrs. at about 45 psi and 80° C. The mixture was filtered and the filtrate concentrated. The residue was diluted to 30 ml. with ethanol and 2.5 g. of methanesulfonic acid added. The isolated methanesulfonate salt was recrystallized from ethanol. The salt weighed 2.3 g. (37.5%) and melted at 128°–130° C.

Analysis: Calculated for $C_{10}H_{15}NO_4S$: C,48.97; H,6.16; N,5.71. Found: C,48.40; H,6.19; N,5.63.

The compound was also prepared by hydrogenolysis of 1-(α-methylbenzyl)-3-(3-chlorophenoxy)azetidine in isopropyl alcohol using the same type catalyst and conditions.

PREPARATION 12

3-[4-(Trifluoromethyl)phenoxy]azetidine Oxalate

To 24.0 g. (0.075 mole) of 3-[4-(trifluoromethyl) phenoxy]-1(α-methylbenzyl)azetidine in 150 ml. of ethanol was added 0.5 g. of 20% Pd(OH)$_2$ on carbon, and the mixture was hydrogenated for five hours at 80° C. and 45 psi. The mixture was cooled, filtered, and the filtrate concentrated at reduced pressure. The residue was dissolved in ethanol and treated with oxalic acid, and the oxalate salt was recrystallized three times in ethanol. The yield was 3.0 g. (13%) and the salt melted at 176°–178° C.

Analysis: Calculated for $C_{12}H_{12}F_3NO_3$: C,46.91; H,3.94; N,4.56. Found: C,47.07; H,3.96; N,4.59.

The compounds in Preparations 13 to 17 are prepared according to the procedure set forth in detail in Preparations 11 and 12 by hydrogenolysis of the α-methylbenzyl radical attached to the azetidine nitrogen. The physical constants are shown in Table 1.

TABLE 1

| Preparation | R | M.P. °C. | Salt |
|---|---|---|---|
| 13 | 2-CONH$_2$ | 173–75 | CH$_3$SO$_3$H |
| 14 | 3-CF$_3$ | 123–25 | [1]C$_6$H$_{11}$NHSO$_3$H |
| 15 | 2-CF$_3$ | 154–56 | HCl |
| 16 | 3-CONH$_2$ | 160–63 | — |
| 17 | 4-CONH$_2$ | 187–88 | (COOH)$_2$ |

[1]N—cyclohexylsulfamate.

The analytical data of Preparations 13 to 17 are shown in Table 2.

TABLE 2

| Preparation | Empirical Formula | Calculated C | Calculated H | Calculated N | Found C | Found H | Found N |
|---|---|---|---|---|---|---|---|
| 13 | C$_{11}$H$_{16}$N$_2$O$_5$S | 45.42 | 5.59 | 9.72 | 45.48 | 5.65 | 9.45 |
| 14 | C$_{16}$H$_{23}$F$_3$N$_2$O$_4$S | 48.48 | 5.85 | 7.07 | 48.08 | 5.94 | 6.97 |
| 15 | C$_{10}$H$_{11}$ClF$_3$NO | 47.35 | 4.37 | 5.52 | 47.12 | 4.32 | 5.45 |
| 16 | C$_{10}$H$_{12}$N$_2$O$_2$ | 62.49 | 6.29 | 14.57 | 62.06 | 6.13 | 13.98 |
| 17 | C$_{12}$H$_{14}$N$_2$O$_6$ | 51.07 | 5.00 | 9.93 | 51.39 | 5.22 | 9.56 |

PREPARATION 18

When in the procedure of Preparation 2 the following are substituted for 3-[4-(trifluoromethyl)phenoxy]-1-(α-methylbenzyl)azetidine:

3-[4-(methyl)phenoxy]-1-(α-methylbenzyl)azetidine,
3-[4-(methoxy)phenoxy]-1-(α-methylbenzyl)azetidine,
3-[3,5-(dimethoxy)phenoxy]-1-(α-methylbenzyl)azetidine,
3-[3-(fluoro)phenoxy]-1-(α-methylbenzyl)azetidine, and
3-[4-(acetyl)phenoxy]-1-(α-methylbenzyl)azetidine, there are obtained:
3-[4-(methyl)phenoxy]azetidine oxalate,
3-[4-(methoxy)phenoxy]azetidine oxalate,
3-[3,5-(dimethoxy)phenoxy]azetidine oxalate,
3-[3-(fluoro)phenoxy]azetidine oxalate, and
3-[4-(acetyl)phenoxy]azetidine oxalate.

EXAMPLE 1

3-[3-(Trifluoromethyl)phenoxy]-1-azetidinecarboxamide

To a solution of 2.2 g (0.01 mole) of 3-[3-(trifluoromethyl)phenoxy]azetidine in 45 ml of methylene chloride and 45 ml of absolute ethyl alcohol was added 7 g. (0.066 mole) of nitrourea and the mixture was stirred at room temperature for 48 hr. The mixture was filtered. The filtrate was evaporated to dryness and the residue was partitioned between 75 ml methylene chloride and 75 ml water. The water layer was extracted three times with 50 ml of methylene chloride. The methylene chloride extracts were combined and evaporated to dryness. The residue was treated (washed) with a mixture of 1 ml methylene chloride and 20 ml of toluene and filtered. The precipitate was recrystallized from ethanol-water to give pale yellow crystals. The crystals were mixed with 2 ml of methylene chloride and 20 ml toluene and the mixture was heated on a steam bath for 2 hrs. The mixture was stored in a refrigerator for approximately 72 hrs. and filtered to give 1.2 g of the product as white crystalline needles, m.p. 151°–152° C.

Analysis: Calculated for $C_{11}H_{11}N_2O_2F_3$: C,50.77; H,4.26; N,10.77. Found: C,50.72; H,4.25; N,10.74.

EXAMPLE 2

3-[3-(Trifluoromethyl)phenoxy]-1-azetidinecarboxamide

A mixture of 30.6 g (0.141 mole) of 3-[3-trifluoromethyl)phenoxy]azetidine and 42 g (0.321 mole) of nitrourea (80%) in 500 ml of acetone was stirred for 5 days (5 days not required, but convenient) at room temperature. The mixture was filtered and the filtrate concentrated in vacuo. The residue was partitioned between 150 ml of water and 100 ml of ethyl acetate and the layers separated. The aqueous layer was washed with 100 ml of ethyl acetate. The ethyl acetate layers were washed with 75 ml of 5% aqueous sodium hydroxide solution followed by 75 ml of water, dried over sodium sulfate and concentrated in vacuo. The residual oil was crystallized from ethy alcohol-ethyl acetate to give 22 g (60%) substantially the title compound. Recrystallization twice from ethyl alcohol gave 9.9 g of white crystalline solid, m.p. 151°–152.5° C.

Analysis: Calculated for $C_{11}H_{11}N_2O_2F_3$: C,50.77; H,4.26; N,10.76. Found: C,50.90; H,4.29; N,10.71.

EXAMPLE 3

When in the procedure of Example 2 the following are substituted for 3-[3-(trifluoromethyl)phenoxy]azetidine:
3-(phenoxy)azetidine,
3-[2-(trifluoromethyl)phenoxy]azetidine,
3-[4-(methyl)phenoxy]azetidine,
3-[4-(methoxy)phenoxy]azetidine, 3-[3,5-(dimethoxy)phenoxy]azetidine,
3-[3-(fluoro)phenoxy)]azetidine,
2-(3-azetidinyloxy)benzamide,
3-(3-azetidinyloxy)benzamide,
4-(3-azetidinyloxy)benzamide, and
3-[4-(acetyl)phenoxy]azetidine,
there are obtained:
3-(phenoxy)-1-azetidinecarboxamide,
3-[2-(trifluoromethyl)phenoxy]-1-azetidinecarboxamide,
3-[4-(methyl)phenoxy]-1-azetidinecarboxamide,
3-[3,5-(dimethoxy)phenoxy]-1-azetidinecarboxamide,
3-[3-(fluoro)phenoxy]-1-azetidinecarboxamide,
3-[2-(carboxamido)phenoxy]-1-azetidinecarboamide,
3-[3-(carboxamido)phenoxy]-1-azetidinecarboxamide,
3-[4-(carboxamido)phenoxy]-1-azetidinecarboxamide, and
3-[4-(aceto)phenoxy]-1-azetidinecarboxamide.

EXAMPLE 4

3-[4-(Trifluoromethyl)phenoxy]-1-azetidinecarboxamide

A solution of 9.6 g (0.025 mole) of 3-(4-trifluoromethylphenoxy)azetidine 56.66% (contains diphenylmethane) in 50 ml of acetone was treated with 4.22 g (0.045 mole) of nitro urea and 5 ml of water. The mixture washeated on a hot plate until a clear solution was obtained then allowed to cool to ambient temperature during the next 4 hr. The reaction was diluted with 200 ml of ice water and an oil separated (diphenylmethane) which was dissolved in 30/60 petroleum ether and separated. Upon standing, a fine white precipitate formed in the aqueous solution. Filtration yielded 3.6 g of fine white crystals, m.p. 176°–178° C. After drying under 0.5 mmHg vacuum at 80° C., the product weight was reduced to 3.1 g, m.p. 178°–179° C.; yield was 47.7%

Analysis: Calculated for $C_{11}H_{11}N_2O_2$: C,50.74; H,4.26; N,10.77. Found: C,50.72; H,4.24; N,10.72.

PHARMACOLOGY

A comparison was made of anti-convulsant activity of the compound of Example 1 and the prior art methyl analog (U.S. Pat. No. 4,226,861, Example 4) using metrazole as the convulsant by the method of Swinyard (See above citation).

Ninety-six adult female mice weighing 24–32 g were randomly assigned to dosage groups according to the method of Steel, R. G. D. and Torrie, J. H. (1960) in "Principles and Procedures of Statistics," McGraw-Hill Book Company, Inc., pp 99–100, pp 428-31. Each mouse was identified with a color code on its tail. The test compounds were administered as suspensions in 10 ml/kg mouse body weight of 0.5% aqueous methyl cellulose within 15 minutes of preparation of the suspension. Metrazole (pentylenetetrazol) was prepared as a solution in physiological saline. The mice were not fasted prior to the test. Eight mice were tested at each dosage level.

Each mouse received one dose of the test drug in the 0.5% aqueous methylcellulose or the control article (0.5% aqueous methylcellulose alone) intraperitoneally. Metrazole (80 mg/kg S.C.) was then given in a loose fold of skin on the back of the neck; i.e., ½ hr after the test compound or control article was given. Injections were given with a 1-ml glass tuberculin syringe with appropriate size hypodermic needle (27 gauge for solutions; 23 gauge for suspensions). All injections were given in a volume of 10 ml/kg mouse body weight. Each mouse was observed for 30 minutes following Metrazol injection. Failure of the animals to exhibit a threshold seizure (a single episode of clonic spasms at least 5 seconds in duration) was defined as protection. Anticonvulsant data were tabulated as the percent protection, i.e., $$\frac{\text{No. Mice Protected}}{\text{No. Mice Tested}} \times 100.$$

The $ED_{50}$ and (95% confidence limits) and potency ratio were ascertained by the computer-based probit analysis ascribed to Finney, D. J. (1964) *Statistical Method in Biological Assay.*, 2nd Ed., New York. Hefner Publishing Co. Results are in Table A. Statistical analysis of the data indicated no significant difference in anti-convulsant potency between the two compounds.

PHARMACOKINETICS

Tests were conducted in order to compare the apparent half-life of elimination in the animal bloodstream of compounds of the present invention with that of the parent prior art compounds of which they are the metabolites as follows:

A two-way crossover study was conducted on male and female adult mongrel dogs. Each dog, after overnight fasting, received a single oral or intravenous dose of 10 mg/kg of test drug in 75% PEG in water and in such concentration that each dog received 1 ml of solution/kg of body weight. Oral doses were administered by using a glass syringe attached to a Levin ® tube (size 18 French) which served as the stomach tube. Intravenous doses were administered through an Intracath ® Placement Unit (Deseret Co., Sandy, Utah) inserted into the cephalic vein of the forelimb. Blood samples were collected as follows: In each study period, 6 ml samples of whole blood were withdrawn from each dog before administering the dose, i.e., at 0 time, and these samples served as controls. Five ml samples of whole blood were then withdrawn at times of ¼, ½, 1.0, 2.0, 3.0, 4.0, 6.0, 8.0, 10.0, 12.0 and 24 hr. after administration of the drug. The blood samples were centrifuged and the plasma was transferred to storage tubes and retained for analysis. Plasma levels of the test drug in the samples were determined by the HPLC method described by Osman, M. A.; Pinchbeck, F. M.; Cheng, L. K.; and Wright, G. J. described in the Journal of Chromatography, 336 (1981). UV detection at 220 nm was used in the procedure. Internal standard was added to the plasma. The test drug being measured and the internal standard were then extracted from the plasma into a mixture of hexane, methylene chloride and butanol. This organic layer was transferred and evaporated and the residue was dissolved in the mobile phase consisting of 8% tetrahydrofuran - 27% acetonitrile and 65% phosphate buffer (0.05 molar; pH 4.2). The final solution was chromatographed on a Waters ® column $C_{18}$ reverse-phase system, the samples being analyzed in sequential order starting with the 0-hr sample (control) and proceeding to the 24 hr sample for the same animal. Duplicate assays were carried out for each sample and the mean value was recorded. If the range of 2 individual assays exceeded the mean by ±12%, the sample was reassayed and the median value reported.

The mean apparent terminal half-life of elimination for the compound of Example 1 from an average of oral and intravenous testing in the foregoing procedure was found to be 2.4±0.4 hr compared to a value of 1.3±0.4 hr found for the parent compound: N-methyl-3-(3-trifluoromethyl) phenoxy-1-azetidinecarboxamide (Example 4, U.S. Pat. No. 4,226,861).

TABLE A

| Test Compound (a) (In Methylcellulose Suspension) Name | Dose, i.p. mg/kg | Number Protected Number Tested | $ED_{50}$ and (Confidence Limits) mg/kg | Potency and 95% Confidence Limits |
|---|---|---|---|---|
| Control-Methylcellulose alone | none | 0/24 | — | |
| 3-[3-(Trifluoromethyl)phenoxy]-1-azetidinecarboxamide (Example 1) | 45 | 1/8 | 99.2 (66.7–147.5) | 0.92 (0.62–1.38) |
| | 67 | 2/8 | | |
| | 100 | 4/8 | | |
| | 150 | 5/8 | | |
| | 225 | 8/8 | | |
| Prior art Compound - N—Methyl-3-(3-trifluoromethylphenoxy)-1-azetidinecarboxamide (Example 4 of U.S. Pat. No. 4,226,861) | 45 | 1/8 | 90.9 (61.7–137.9) | 1.00 |
| | 67 | 2/8 | | |
| | 100 | 3/8 | | |
| | 150 | 8/8 | | |

Footnotes:
(a) All mice were first injected with 10 ml/kg of 0.5% aqueous methylcellulose intraperitoneally in which test compound was suspended if present.
(b) 80 mg/kg Metrazole in 10 ml saline of mouse body weight was administered to all mice subcutaneously in a loose fold of skin on the back of the neck one-half hr. after administration of test compound.

FORMULATION AND ADMINISTRATION

The pharmacologically active 3-phenoxy-1-azetidinecarboxamides of this invention are effective in the treatment of both petit mal epilepsy and grand mal epilepsy. Effective quantities of these compounds may be administered to a living animal body orally as in capsules, tablets or elixirs. It is only necessary that the active ingredient constitute an effective amount, i.e., such that a suitable effective dosage will be obtained consistent with the dosage form employed. The exact individual dosage as well as daily dosages will, of course, be determined according to standard medical principles under the direction of a physician or veterinarian.

Based upon a comparison with known anticonvulsant compounds, daily dosages appear to preferably range from about 0.5 to 1.5 milligrams per kilogram of body weight in the treatment of petit mal epilepsy and about 25 to 35 milligrams per kilogram of body weight in the treatment of grand mal epilepsy. Very small quantities of the active materials of the present invention, even as low as 0.1 milligram, are effective when minor therapy is involved. Unit dosages are usually 5 milligrams or above and preferably 25, 50 or 100 milligrams per unit dose. The active ingredients of the invention may be combined with other pharmacologically active agents as previously indicated, or with buffers, antacids or the like, for administration and the proportion of the active agent in the composition may be varied widely.

CAPSULES

Capsules of 5 mg., 25 mg., and 50 mg. of active ingredient per capsule are prepared; with higher amounts of ingredient reduction may be made in the amount of lactose.

| Typical blend for encapsulation | Per Capsule, mg. |
|---|---|
| Active ingredient | 5.0 |
| Lactose | 296.7 |
| Starch | 129.0 |
| Magnesium stearate | 4.3 |
| Total | 435.0 mg. |

Uniformly blend the selected active ingredient with lactose, starch and magnesium stearate and encapsulate the blend.

Additional capsule formulations preferably contain a higher dose of active ingredient and are as follows:

| Ingredients | 100 mg. per Capsule | 250 mg. per Capsule | 500 mg. per Capsule |
|---|---|---|---|
| Active ingredient | 100.0 | 250.0 | 500.0 |
| Lactose | 231.5 | 126.5 | 31.1 |
| Starch | 99.2 | 54.2 | 13.4 |
| Magnesium stearate | 4.3 | 4.3 | 5.5 |
| Total, mg. | 435.0 | 435.0 | 550.0 |

TABLETS

A typical formulation for a tablet containing 5.0 mg. of active ingredient per tablet follows. The formulation may be used for other strengths of active ingredient by adjustment of weight of dicalcium phosphate.

| Ingredients | Per Tablet, mg. |
|---|---|
| (1) Active ingredient | 5.0 |
| (2) Corn Starch | 13.6 |
| (3) Corn Starch (paste) | 3.4 |
| (4) Lactose | 79.2 |
| (5) Dicalcium phosphate | 68.0 |
| (6) Calcium Stearate | 0.9 |
| Total | 170.1 mg. |

Uniformly blend 1, 2, 4 and 5. Prepare 3 as a 10 percent paste in water. Granulate the blend with the starch paste and pass the wet mass through a number eight mesh screen. The wet granulation is dried and passed through a number twelve mesh screen. The dried granules are blended with calcium stearate and compressed.

Additional tablet formulations preferably contain a higher dosage of the active ingredient and are as follows.

| 50 mg. Tablet | |
|---|---|
| Ingredients | Per Tablet, mg. |
| Active ingredient | 50.0 |
| Lactose | 90.0 |
| Milo starch | 20.0 |
| Corn starch | 38.0 |
| Calcium stearate | 2.0 |
| Total | 200.0 |

Uniformly blend the active ingredient, lactose, milo starch and corn starch. The blend is granulated, using water as a granulating medium. The wet granules are passed through an eight mesh screen and dried at 140 to 160 degrees Fahrenheit overnight. The dried granules are passed through a number ten mesh screen and blended with the proper amount of calcium stearate and this blend is then converted into tablets on a suitable tablet press.

What is claimed is:

1. A method of treatment for anticonvulsant effect which comprises orally administering to a mammal an effective amount of a compound selected from the group consisting of 3-phenoxy-1-azetidinecarboxamides having the formula:

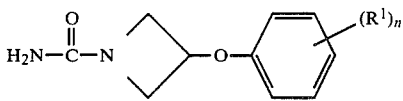

wherein;
$R^1$ is selected from the group consisting of hydrogen, fluoro, loweralkyl, loweralkoxy, trifluoromethyl, acetyl, or aminocarbonyl; and
n is selected from 1 to 3 inclusive wherein $R^1$ may be the same or different.

2. The process of claim 1 wherein the compound is 3-[3-(trifluoromethyl)phenoxy]-1-azetidinecarboxamide.

3. The process of claim 1 wherein the compound is 3-[4-(trifluoromethyl)phenoxy]-1-azetidinecarboxamide.

* * * * *